United States Patent
Wong et al.

(10) Patent No.: US 6,334,848 B1
(45) Date of Patent: Jan. 1, 2002

(54) REMOTE PEDOMETER

(75) Inventors: Philip Lim-Kong Wong, Kettering (GB); Ka Yiu Sham, Great Falls, VA (US); Robert Fabrizio, Norwalk, CT (US)

(73) Assignee: Acumen, Inc., Sterling, VA (US)

( * ) Notice: Subject to any disclaimer, the term of this patent is extended or adjusted under 35 U.S.C. 154(b) by 0 days.

(21) Appl. No.: 09/480,678

(22) Filed: Jan. 11, 2000

(51) Int. Cl.[7] .......................... A61B 5/02; A61B 5/103; A61B 5/117

(52) U.S. Cl. ....................... 600/481; 600/595; 600/587; 600/503

(58) Field of Search .............................. 600/481, 300, 600/483, 500, 502, 503, 587, 595

(56) References Cited

U.S. PATENT DOCUMENTS

| 4,367,752 A | * | 1/1983 | Jimenez et al. | 600/502 |
|---|---|---|---|---|
| 4,566,461 A | * | 1/1986 | Lubell et al. | 600/481 |
| 4,855,942 A | * | 8/1989 | Bianco | 702/160 |
| 4,962,469 A | * | 10/1990 | Ono et al. | 702/160 |
| 5,539,706 A | * | 7/1996 | Takenaka et al. | 600/503 |
| 5,891,042 A | | 4/1999 | Sham et al. | |
| 6,163,718 A | * | 12/2000 | Fabrizio | 600/519 |
| 6,175,608 B1 | * | 1/2001 | Pyles et al. | 377/24.2 |

* cited by examiner

Primary Examiner—Eric F. Winakur
Assistant Examiner—Navin Natnithithadha
(74) Attorney, Agent, or Firm—Crowell & Moring LLP

(57) ABSTRACT

A fitness monitoring device, comprising a wrist-based device including a receiver and a display; a separate, remote, pedometer including pedometer step sensing circuitry and wireless transmission circuitry; and wherein said pedometer step sensing circuitry senses a user's steps and said remote pedometer wirelessly transmits a signal corresponding to said sensed steps to said wrist-based device, and further wherein said wrist-based device processes the wirelessly transmitted signal received by said receiver and controls the display.

6 Claims, 5 Drawing Sheets

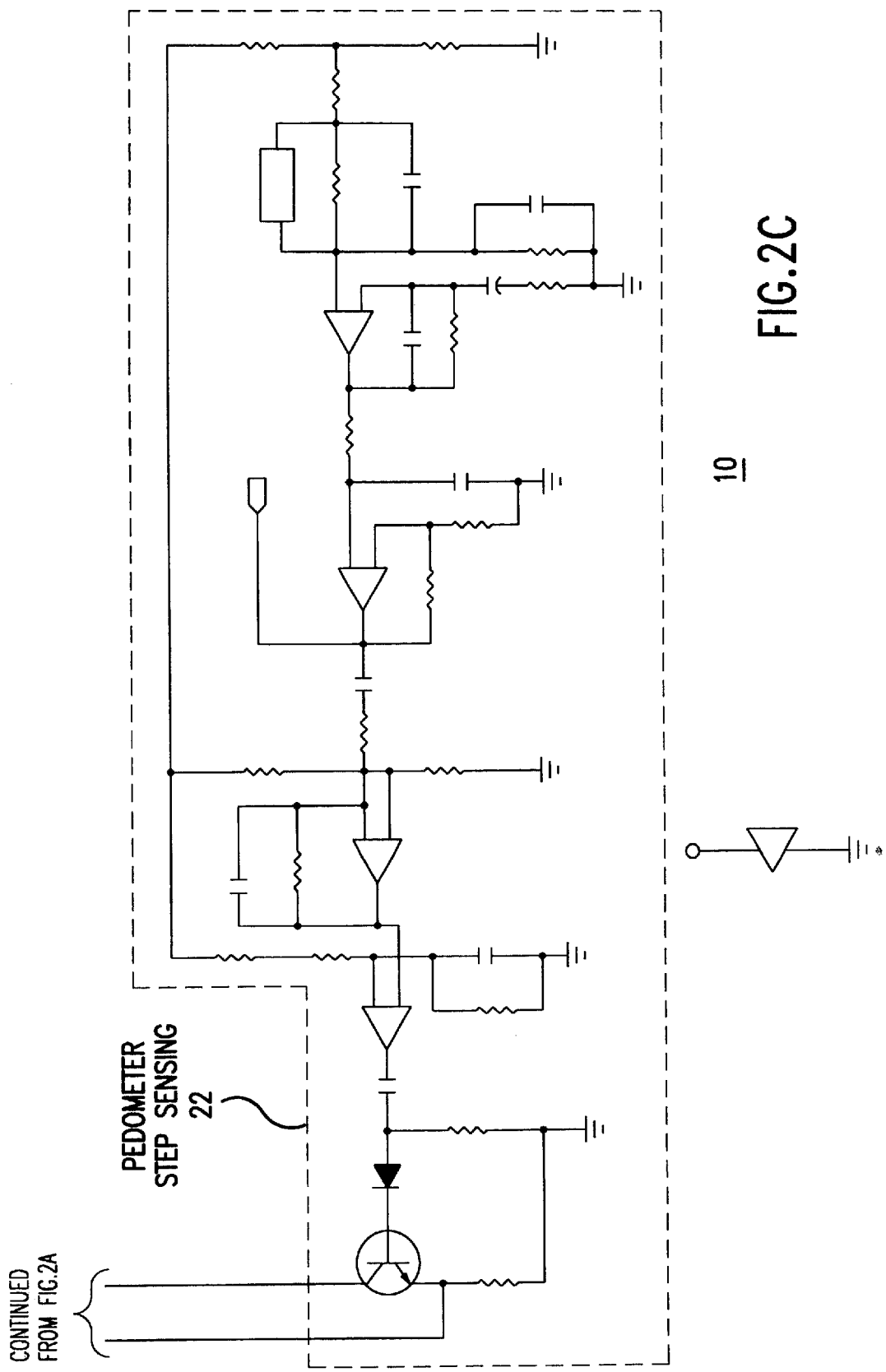

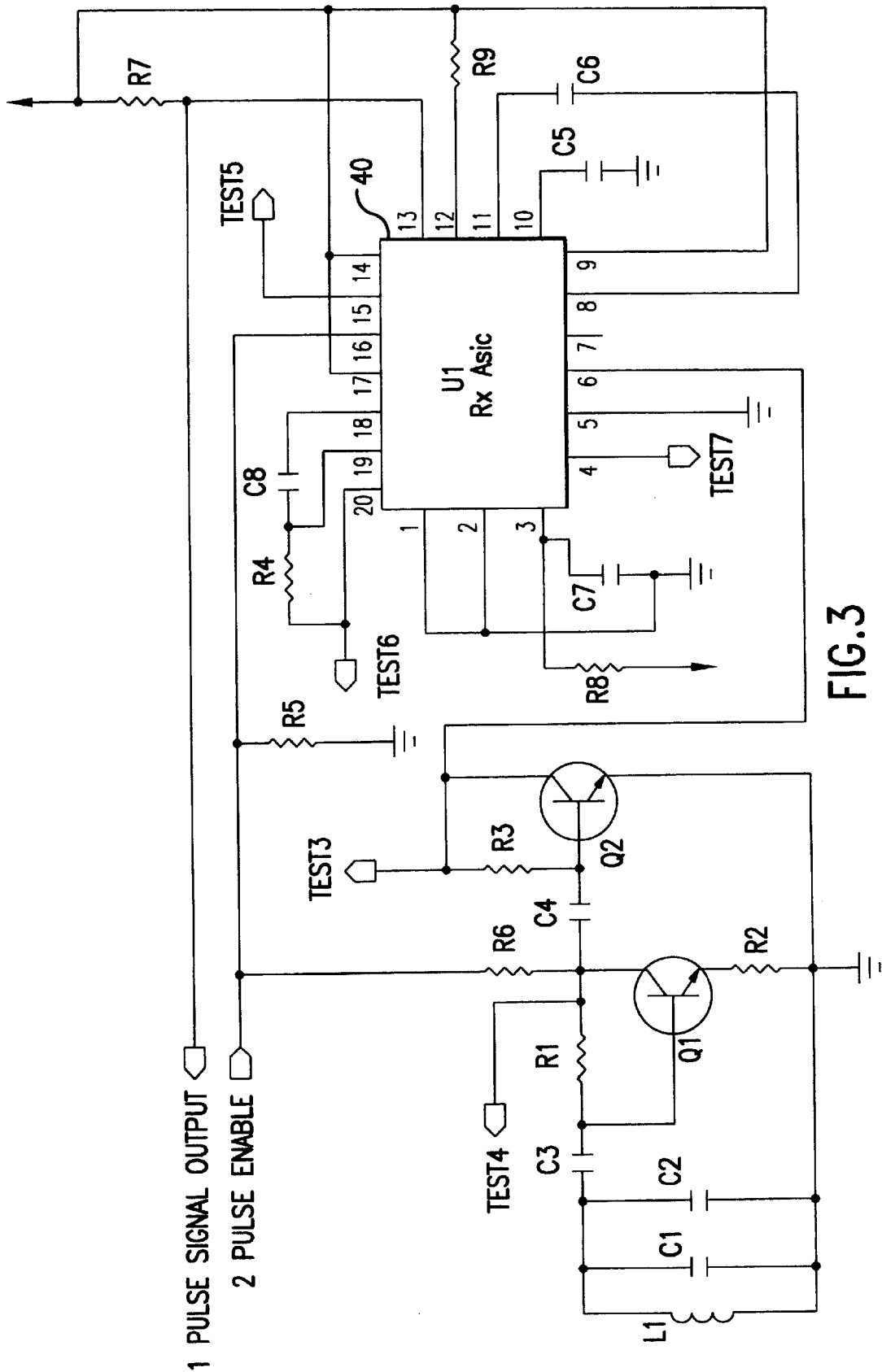

REMOTE PEDOMETER

BACKGROUND AND SUMMARY OF THE INVENTION

The invention relates to a fitness monitoring device and, more particularly, to a pedometer which records the distance a walker or a jogger covers by responding to the user's body motion at each step.

To measure the walking or jogging distance covered by a user, both mechanical and electronic pedometers have been developed. Such pedometers consist of mechanical or electronic circuits which sense the body motion of the user at each step. Typically, such pedometers are worn on the side of the user such as by being clipped to a belt or the waistline of the user's pants in the manner of a pager or the like. Other known pedometers are worn on a user's wrist.

Commonly assigned U.S. Pat. No. 5,891,042 provides one example of a fitness monitoring device having an electronic pedometer in combination with a wireless heart rate monitor. In this patent, an electronic pedometer is formed as part of the circuit which receives the wirelessly transmitted heart rate signals. As shown in FIG. 1 of U.S. Pat. No. 5,891,042, the fitness monitoring device, which includes the electronic circuitry of the pedometer integrated together with or without a wireless heart rate monitor, is clipped to a user's waistband.

In general, both mechanical and electrical pedometers include two components, a first of which is designed to sense the steps of the user, and the second of which processes signals indicative of the steps into useful information. As shown in U.S. Pat. No. 5,891,042, a microprocessor is used to process the information signals and is integrated with the step sensing circuitry either in a unit designed to be clipped onto the user's waist or in a form strapped to a user's wrist. Such known pedometers, however, are oftentimes disadvantageous, especially when worn as a watch-type of device on a user's wrist. This is because the required circuitry, especially for electronic pedometers, tends to consume a large amount of space and energy, thus requiring a bulkier wrist-based device accommodating a sufficiently sized battery. When the wrist-based device is combined with other sensing functions, such as a wireless heart rate monitor, watch functions, etc., the problem is further aggravated.

There is therefore needed a pedometer which overcomes the above problems. This and other needs are met by the present invention which provides a remote pedometer in which the pedometer sensor signal is wirelessly transmitted to a wrist-based device, such as a watch-type of device for display to the user. This wireless transmission of the pedometer sensor signal allows the step sensing function of the pedometer to be separated from the processing function. As a result, the step sensing function can be performed by a circuit in a unit which clips to a user's waistband, socks, shoes, etc. The output signals can be wirelessly transmitted to a wrist-based watch device for processing and more convenient display.

By providing such a remote pedometer, the wrist-based device can be made more compact and simpler, while allowing more functions to be incorporated therein. Furthermore, by separating the step sensing function from the processing function, separate batteries can be provided to perform each function, which leads to an increased operating life of the system.

Heretofore it has been unknown to provide a remotely located pedometer which wirelessly transmits its signal to a wrist-based device for display and interpretation. Of course, such a remote pedometer can be combined with a wireless heart rate monitor or other devices.

Other objects, advantages and novel features of the present invention will become apparent from the following detailed description of the invention when considered in conjunction with the accompanying drawings.

BRIEF DESCRIPTION OF THE DRAWINGS

FIG. 3 is a circuit diagram of the receiver in the wrist-based device.

DETAILED DESCRIPTION OF THE DRAWINGS

Figure 1:
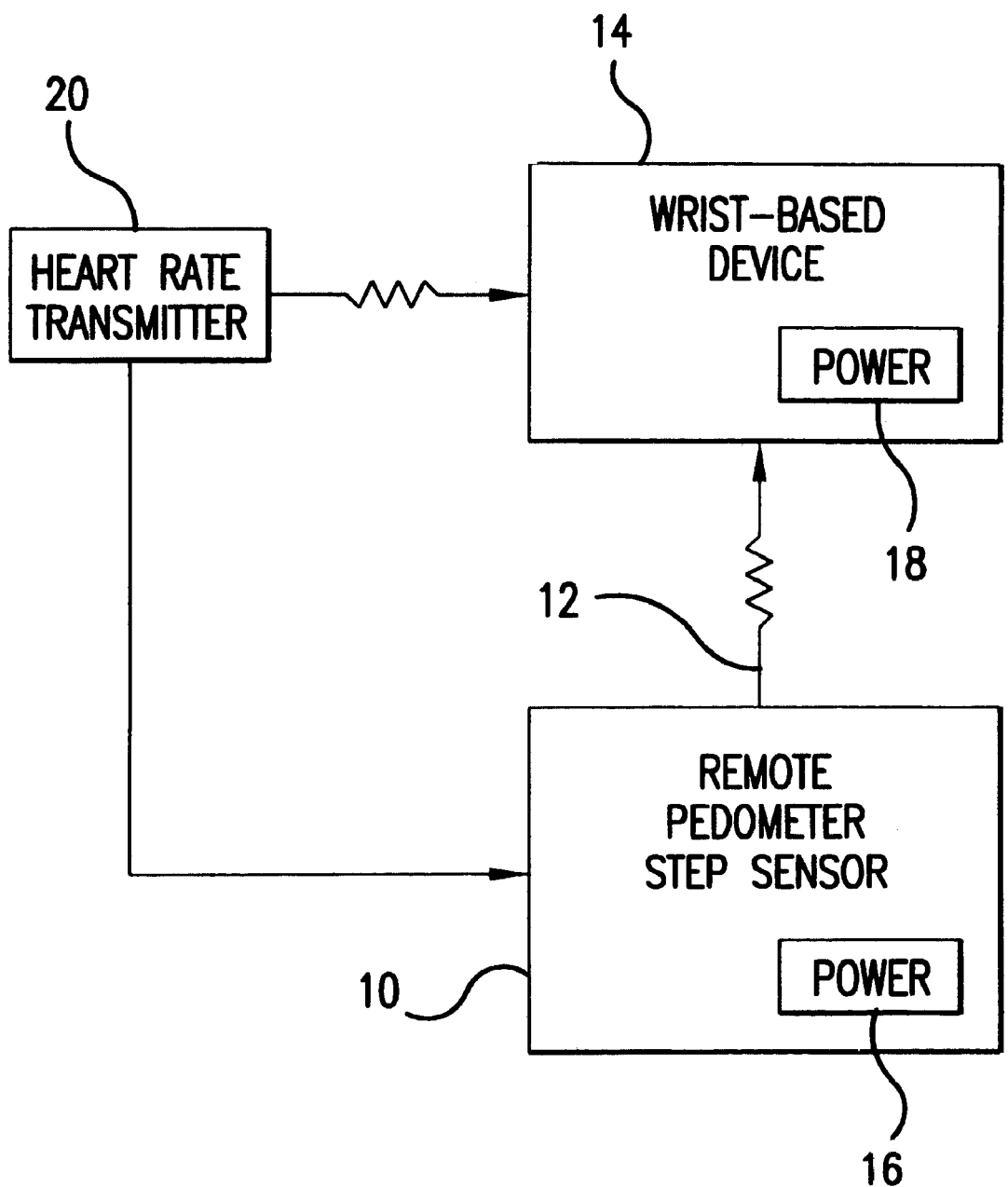
FIG. 1 is a schematic block diagram of a remote pedometer according to the present invention.

Referring to FIG. 1, a remote pedometer step sensor 10 is shown in block diagram form. The remote pedometer wirelessly transmits its step sensing signals 12 to a wrist-based device 14. The wrist-based device 14 can be, for example, in a watch form, incorporated into a watch, and/or combined together with other devices such as a heart rate monitor, which receives heart rate signals from a heart rate transmitter 20.

By remotely locating the pedometer 10, a separate power supply 16 can be provided in addition to the power source 18 located in the wrist-based device. Of course, the wrist-based device 14 is provided with some type of display or other indicator in order to provide useful information to the user.

Figure 2A:
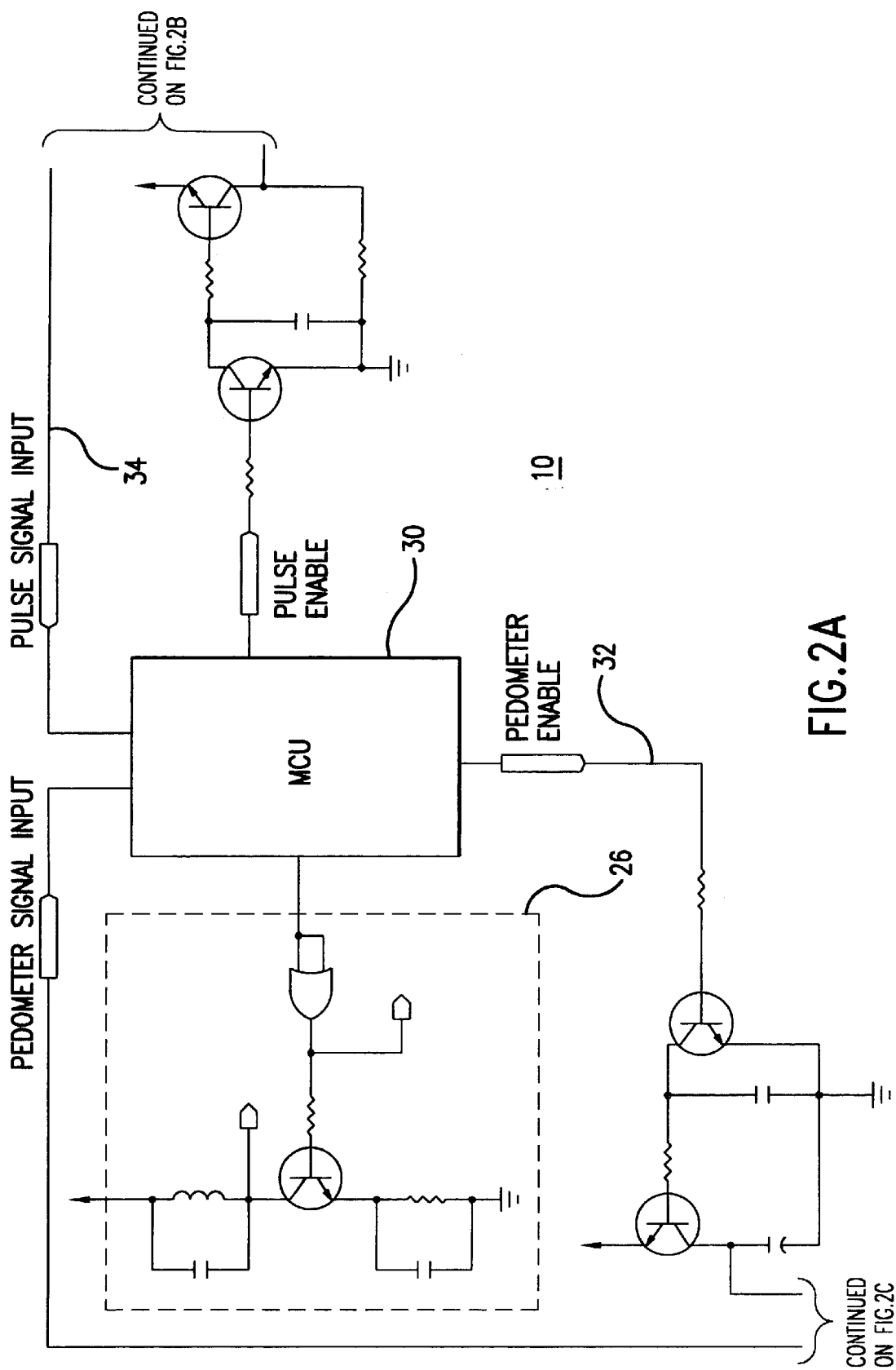
FIG. 2 is a circuit diagram of the pedometer step sensing function and its wireless transmission to the processing function.
Figure 2B:
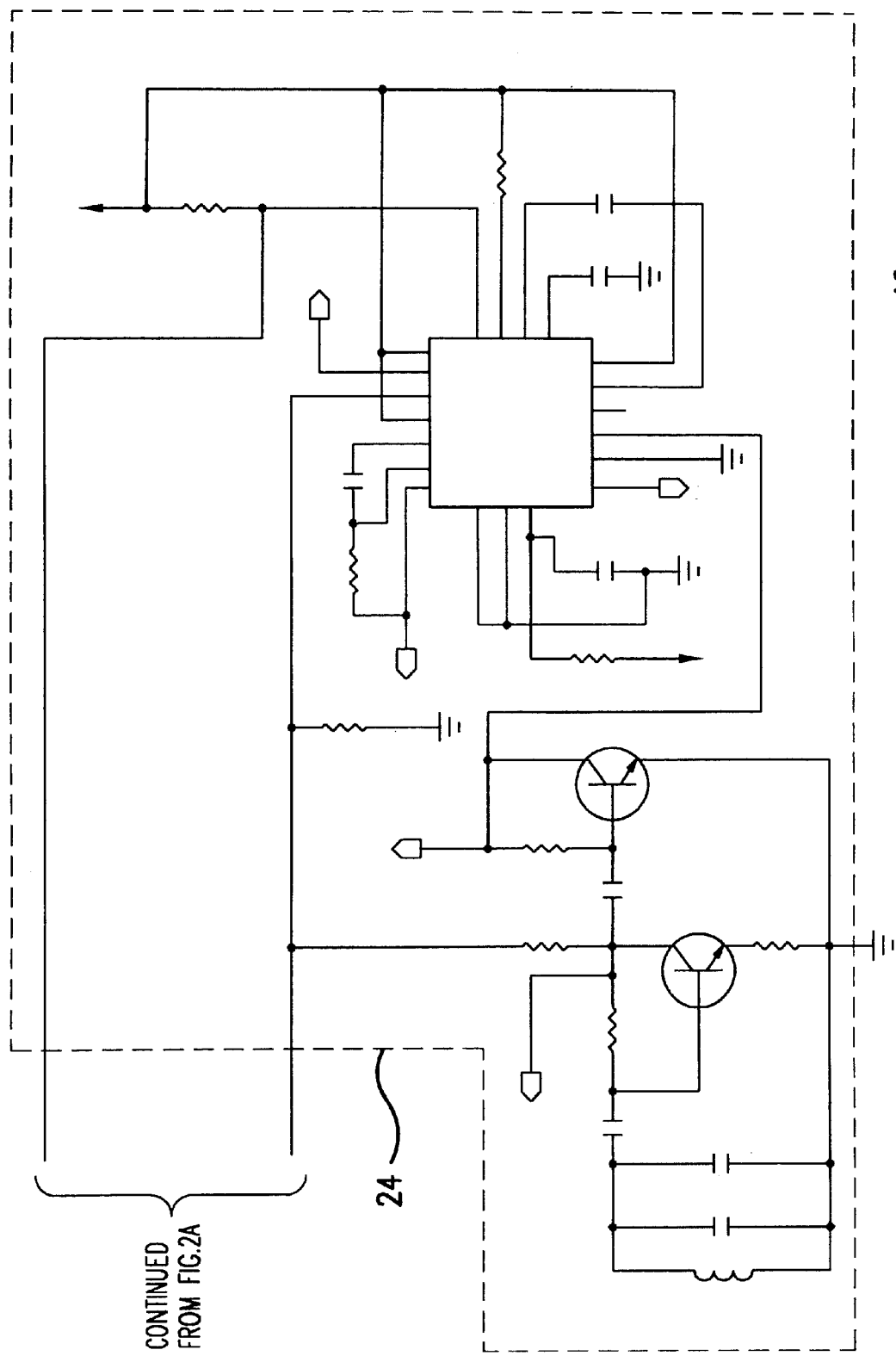

Referring to FIG. 2, there is shown a circuit diagram of the remote pedometer and its wireless coupling with a wrist-based device. The remote pedometer 10 includes pedometer step sensing circuitry 22, a receiver 24 for synchronization with a heart-rate transmitter and a wireless transmission circuit 26. The wireless receiver circuitry 24 functions to "lock-on" to transmissions from the wireless heart-rate transmitter for synchronization. Upon detecting the heart-rate pulse transmission from the wireless heart-rate transmitter, such as a heart-rate transmitter belt, the remote pedometer 10 is considered to be in synchronization with the heart-rate transmitter. The remote pedometer 10 then time multiplexes the sensed steps for transmission to the wrist-based device 14. As such, heart-rate pulses from the wireless heart-rate transmitter and steps from the remote pedometer share the same transmission frequency channel but, are timewise separated via the synchronized transmission. The control unit 30 in the remote pedometer 10 operates to receive the step signals 32 and synchronization pulse signals 34 in order to perform the time-multiplex transmissions via the transmission circuitry 26.

Referring to FIG. 3, there is shown the receiver circuitry in the wrist-based device 14. The ASIC 40 receives the signal time-multiplexed channel transmissions from the remote pedometer 10.

By remotely locating the pedometer apart from the wrist-based device, it is also possible to use a simpler and less expensive mechanical pedometer as opposed to an electronic one, especially when the wrist-based device is combined with other monitoring systems. With the step sensing function 10 arranged remotely from the processing function, electronic interference which otherwise may occur between a mechanical step sensor due to electronic noise emitted at each mechanically sensed step (that would interfere with other electronic circuits in the wrist-based device, such as a wireless heart rate monitor) can be eliminated.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A fitness monitoring device, comprising:

a wrist-based device including a receiver and a display;

a separate, remote, pedometer including pedometer step sensing circuitry and wireless transmission circuitry;

wherein said pedometer step sensing circuitry senses a user's steps and said remote pedometer wirelessly transmits a signal corresponding to said sensed steps to said wrist-based device, and further wherein said wrist-based device processes the wirelessly transmitted signal received by said receiver and controls the display;

a wireless heart-rate transmitter; and wherein said remote pedometer further comprises a receiver circuit which receives transmissions from said wireless heart-rate transmitter for synchronizing the wireless heart-rate transmissions with the wireless step sensing transmissions.

2. The fitness monitoring device according to claim 1, wherein said wireless heart-rate transmitter and said wireless transmission circuitry of said remote pedometer share a single transmission frequency channel in a time-multiplexed manner.

3. The fitness monitoring device according to claim 1, wherein said wrist-based device and said remote pedometer have separate power supplies.

4. The fitness monitoring device according to claim 2, wherein said wrist-based device and said remote pedometer have separate power supplies.

5. The fitness monitoring device according to claim 1, further comprising watch functions incorporated into said wrist-based device.

6. The fitness monitoring device according to claim 2, further comprising watch functions incorporated into said wrist-based device.

* * * * *